(12) United States Patent
Adell

(10) Patent No.: US 9,911,363 B1
(45) Date of Patent: Mar. 6, 2018

(54) DENTAL ARCH MODELS

(71) Applicant: Loren S. Adell, Sunnyvale, TX (US)

(72) Inventor: Loren S. Adell, Sunnyvale, TX (US)

(73) Assignees: Loren S. Adell, Sunnyvale, TX (US); Michael Adell, Sunnyvale, TX (US)

( * ) Notice: Subject to any disclaimer, the term of this patent is extended or adjusted under 35 U.S.C. 154(b) by 80 days.

(21) Appl. No.: 15/181,675

(22) Filed: Jun. 14, 2016

Related U.S. Application Data

(63) Continuation of application No. 13/775,774, filed on Feb. 25, 2013, now Pat. No. 9,378,660.

(51) Int. Cl.
*A61C 11/00* (2006.01)
*G09B 23/28* (2006.01)
*G09B 23/34* (2006.01)
*G09B 23/32* (2006.01)
*G09B 23/30* (2006.01)

(52) U.S. Cl.
CPC ............ *G09B 23/283* (2013.01); *A61C 11/00* (2013.01); *G09B 23/28* (2013.01); *G09B 23/30* (2013.01); *G09B 23/32* (2013.01); *G09B 23/34* (2013.01)

(58) Field of Classification Search
CPC ........ G09B 23/28; G09B 23/32; G09B 23/34; G09B 23/283; G09B 23/30; A61C 11/00
See application file for complete search history.

(56) References Cited

PUBLICATIONS

"Paradigm Dental Demonstration Models," https://web.archive.org/web/20030908173641/http://www.paradigmmodels.com/products.html, Sep. 8, 2003.*

* cited by examiner

*Primary Examiner* — Jack Yip
*Assistant Examiner* — Jennifer L Korb
(74) *Attorney, Agent, or Firm* — George L. Boller

(57) ABSTRACT

An arch model has a set of teeth and a wall which bridges the set of teeth and has a surface opposite the set of teeth. A cover which contains informational material about the dental arch model separably attaches to the wall of the dental arch model. Different informational material can be presented by removing the cover and replacing it with another cover which contains the different informational material.

14 Claims, 5 Drawing Sheets

DENTAL ARCH MODELS

TECHNICAL FIELD

This invention relates to dentistry. In particular the invention relates to dental arch models.

BACKGROUND

There are various types of dental arch models. One type is known as a typodont.

A typodont is a synthetic life-like model of ideal upper and lower dental arches which can be articulated between closed and open conditions. Typodonts are used for various purposes including teaching, demonstration, and/or advertisement of dental products such as orthodontic appliances.

A manufacturer of orthodontic appliances may advertise its products by mounting them on teeth of a typodont. For identifying a manufacturer, a typodont may contain information such as the manufacturer's name and/or logo. The information is typically placed to be seen when a person views a top surface of the typodont's upper dental arch. The information is made permanent by embedding it in the typodont at time of fabrication.

The fabrication process comprises placing a sheet containing printed information on a surface of one of the dental arch models, typically on a top surface of the upper arch model, and then overmolding at least the informational sheet with transparent material. Once the overmold material has set to a hardened condition, the sheet material becomes trapped in place and can be viewed through the transparent material.

Another type of dental arch model comprises a single arch, either an upper arch or a lower arch. The model may contain an ideal dental arch or it may be an irregular dental arch which can be used for educational purposes.

SUMMARY OF THE INVENTION

Because the commercial typodont which has just been described encapsulates the sheet of information inside the finished typodont, the sheet cannot be removed and replaced without damaging or destroying the typodont.

Briefly, this disclosure introduces a typodont which allows informational material to be displayed on one of its two dental arch models without overmolding. The informational material is disposed on a removable cover which separably attaches to one of the two dental arch models. Because the cover separably attaches to the dental arch model, it can be removed and replaced by another cover which has different informational material without damaging the dental arch model. Because a typical dental arch model, even when mass-produced on a small scale, is not inexpensive, applicant provides an economical way to re-use the dental arch model when different informational material is to be shown.

The cover is placed over a wall of the dental arch model to which the cover separably attaches. The informational material is present on one of an inner surface of the cover which confronts the wall of the dental arch model, and an outer surface of the cover which is opposite the inner surface.

The foregoing summary, accompanied by further detail of the disclosure, will be presented in the Detailed Description below with reference to the following drawings that are part of this disclosure.

DETAILED DESCRIPTION

Figure 1:
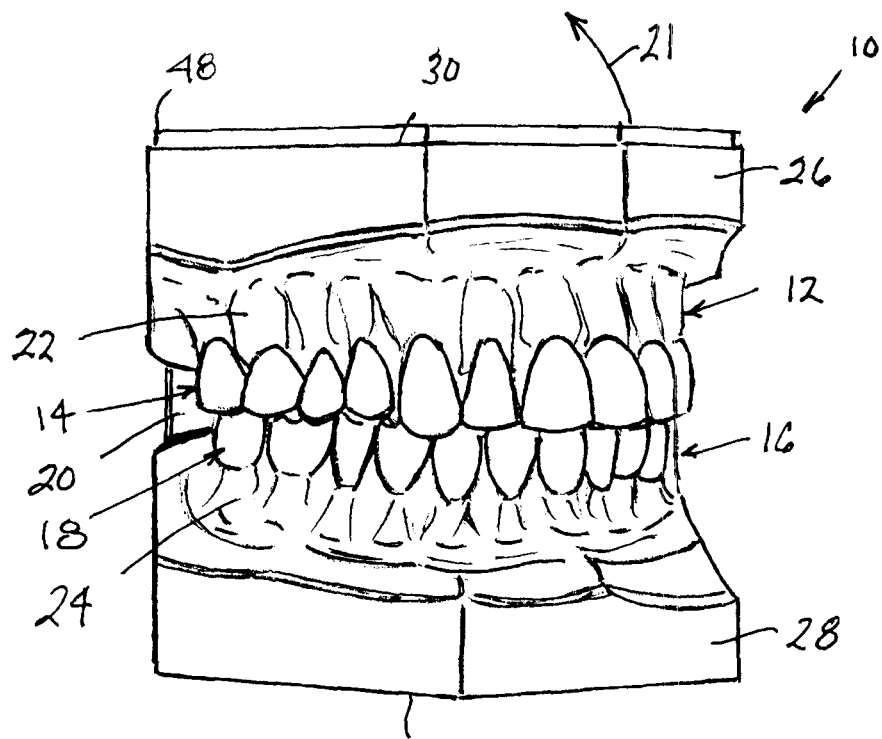
FIG. 1 is a perspective view of a typodont.
Figure 2:
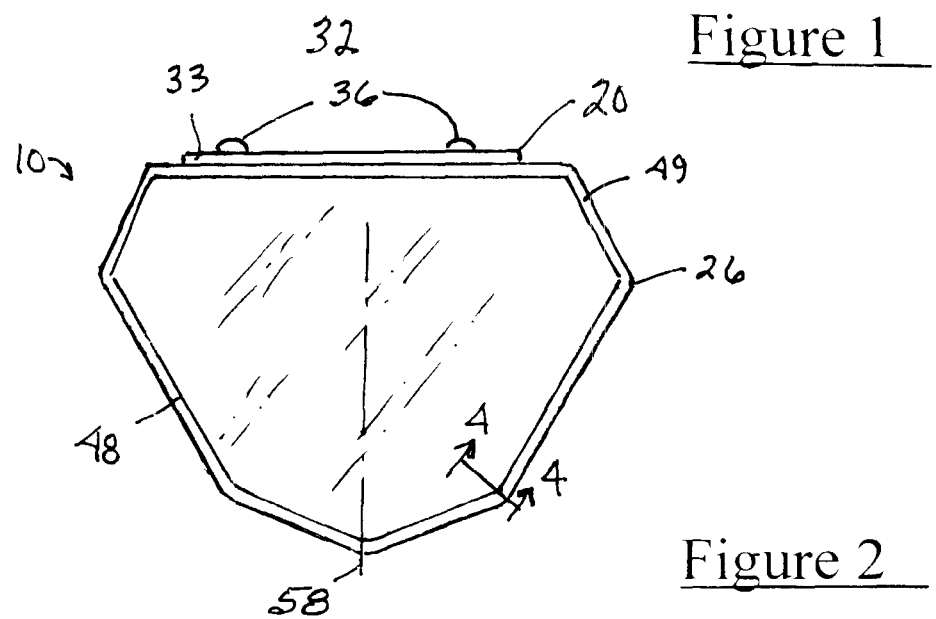
FIG. 2 is a top plan view of the typodont of FIG. 1.
Figure 3:
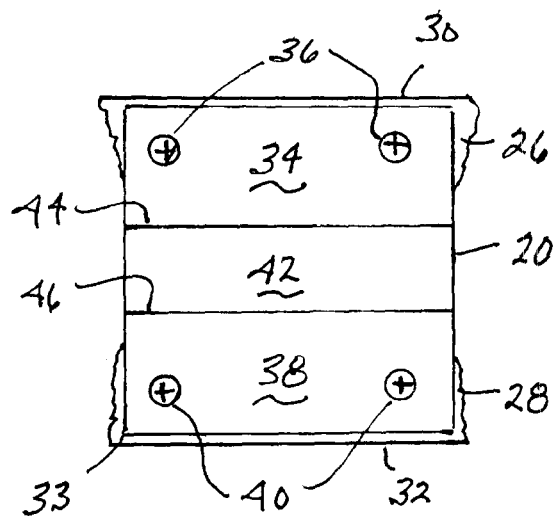
FIG. 3 is a rear view of the typodont of FIG. 1.
Figure 4:
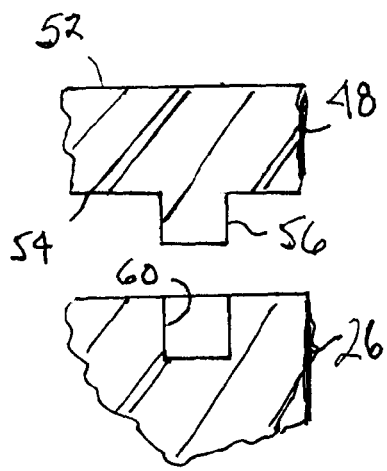
FIG. 4 is an enlarged cross section view in the direction of arrows 4-4 in FIG. 2.

FIGS. 1-7 show an embodiment of a typodont 10 comprising an upper arch model 12 having a set of upper teeth 14 and a lower arch model 16 having a set of lower teeth 18, and a connection 20 for articulating the arches between closed condition shown in FIG. 1 and open condition, suggested by arrow 21 representing swinging motion of upper arch model 12 away from lower arch model 16.

Each set of teeth 14, 18 is fixedly set in a model of the respective gum 22, 24. Each gum 22, 24 is bridged by a respective wall 26, 28 opposite the respective set of teeth 14, 18. Wall 26 has a flat top end surface 30 opposite set of upper teeth 14 and a side surface extending around the perimeter of top end surface 30. Wall 28 has a flat bottom surface 32 opposite set of lower teeth 18 and a side surface extending around the perimeter of bottom wall 32.

Connection 20 comprises a sheet 33 of synthetic material having a flat upper zone 34 fastened to wall 26 posteriorly of its set of teeth by fasteners 36 and a flat lower zone 38 fastened to wall 28 posteriorly of its set of teeth by fasteners 40. Upper zone 34 and lower zone 38 join with opposite sides of a central zone 42 by upper and lower living hinge joints 44, 46 which provide for articulation of the arches by allowing sheet 33 to flex.

A cover 48 is separably attached to upper arch model 12 and covers the entirety of top end surface 30 except for a small margin 49 of the continuous perimeter of top end surface 30. Cover 48 has a continuous perimeter which substantially congruently registers with the continuous perimeter of top end surface 30. Cover 48 has a uniform thickness between a top, or outer, surface 52 and a bottom, or inner, surface 54 except at the locations of posts 56 which extend from bottom surface 54 to make the distance from top surface 52 to the end of each post 56 greater.

In the particular typodont illustrated, the perimeters of top surface 30 and cover 48 are symmetrical about the median body plane 58 and each has seven sides. Posts 56 are arranged in a trapezoidal pattern which is symmetric about median plane 58 with two posts on each side of the median plane. Each post is set inwardly from the perimeter of cover 48 at the intersection of a respective pair of sides.

Top end surface 30 has four blind holes 60 arranged in a trapezoidal pattern matching that of posts 56. Posts 56 fit within holes 60 to provide cover 48 with a friction or force fit to wall 26. The friction or force fit holds cover 48 on wall 26 over top surface 30 while allowing the cover to be separated from the wall by prying the cover off. For example, cover 48 may be separated manually by inserting one's fingernail between the perimeters of the cover and the wall and prying the cover away.

Figure 6:
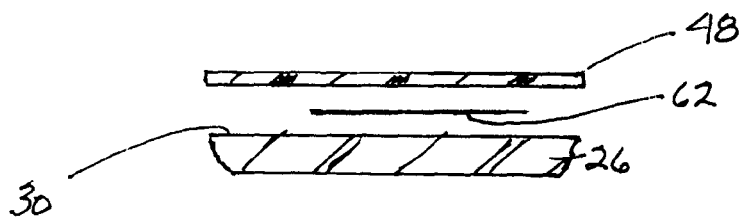
FIG. 6 is an exploded cross section view in the direction of arrows 6-6 in FIG. 7.
Figure 5:
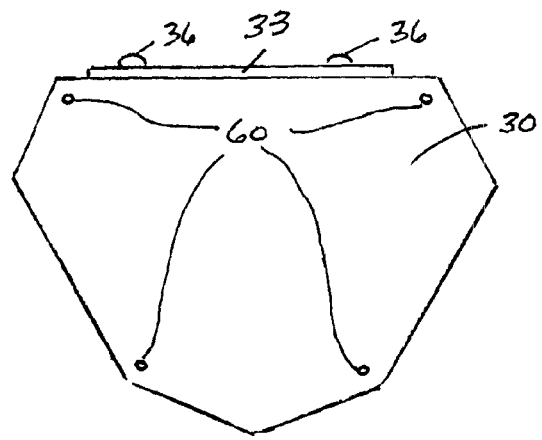
FIG. 5 is a view in the same direction as FIG. 2 but with a part having been removed.
Figure 7:
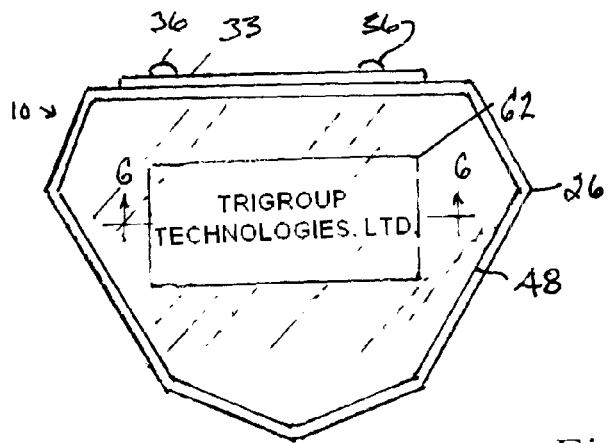
FIG. 7 is a view looking in the same direction as FIG. 2 but including an additional part.

Cover 48 is also transparent for allowing an element disposed between it and top end surface 30 to be seen. FIGS. 6 and 7 show such an element as a flat sheet 62 containing indicia such as a company name, a product name, a design, or a logo. Sheet 62 is placed between top end surface 30 and cover 48 as shown in FIG. 6 and the cover is attached to wall 26 by inserting posts 56 into holes 60, thereby trapping sheet 62 between cover 48 and wall 26. As shown by FIG. 7, the indicia on sheet 62 can be read or viewed through the transparent material of the cover.

Figure 8:
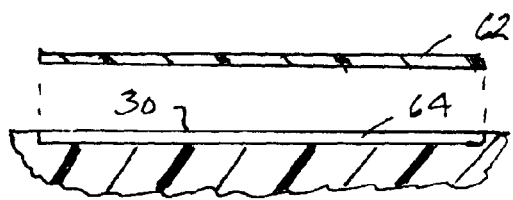
FIG. 8 is a view similar to FIG. 6, but showing another embodiment.

Sheet 62 can be properly located in any suitable manner on top end surface 30 before cover 48 is attached to wall 26. FIG. 8 shows one possibility, a shallow recess 64 in top surface 30 having a shape for receiving and locating sheet 62. Alternatively a similar recess could be provided in the bottom of cover 48 instead and the sheet placed there. For example, sheet 62 can be a mylar sheet having a thickness of about 0.004 inch. A thicker sheet can be accommodated by increasing the depth of the cavity, or by two shallower cavities in confronting surfaces of the cover and the upper arch model. Instead of posts 56 being integral with cover 48 and holes 60 being in upper arch model 12, posts may be in the upper arch model and the holes in the cover.

Figure 9:
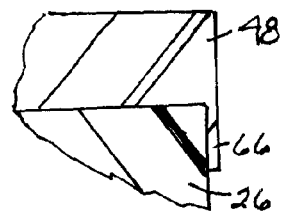
FIG. 9 is a view similar to FIG. 4, but showing still another embodiment.
Figure 10:
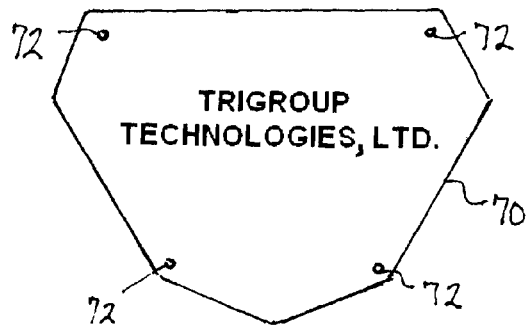
FIG. 10 is a top plan view of a different part which can be used with the typodont of FIG. 1.
Figure 11:
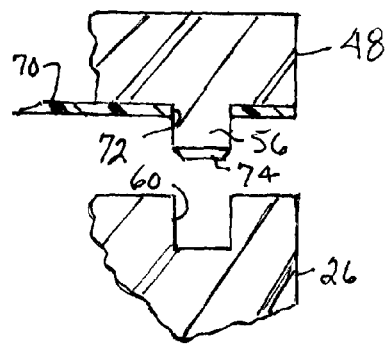
FIG. 11 is a fragmentary view similar to FIG. 4 showing use of the part of FIG. 10.

Instead of using posts and holes for separably attaching cover 48 to upper arch model 12, FIG. 9 shows a short narrow flange 66 extending around the perimeter of cover 48 and overlapping the side of wall 26. Cover 48 has a continuous perimeter which is still substantially congruent with the continuous perimeter of top surface 30 but now slightly overhangs the side of wall 26. Flange 66 is dimensioned to provide a friction fit against the side of wall 26. The flange may be continuous or discontinuous. FIG. 10 shows a flat sheet 70 intended to be placed between top end surface 30 and cover 48. Sheet 70 has a shape essentially congruent with top surface 30 and cover 48. Sheet 70 contains four holes 72 located to allow the sheet to be properly aligned for congruity with both top end surface 30 and cover 48 by aligning the holes 72 with posts 56 arranged in a matching pattern on cover 48 and inserting the posts into the holes as shown in FIG. 11. The posts can then be inserted into holes 60 in top end surface 30 to create a final product having sheet 70 securely located and captured. FIG. 11 shows posts 56 to have tapered leads, or chamfers, 74 for facilitating their insertion into holes 60.

Figure 12:
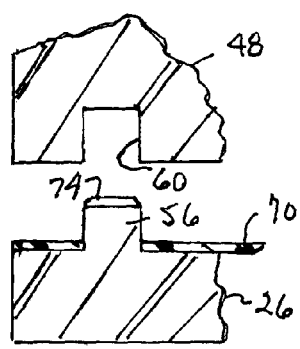
FIG. 12 is a fragmentary view showing a variation on FIG. 11.

FIG. 12 shows a reversal of the posts 56 and the holes 60 with the posts projecting from top end surface 30 of wall 26 and the holes being in cover 48.

Figure 13:
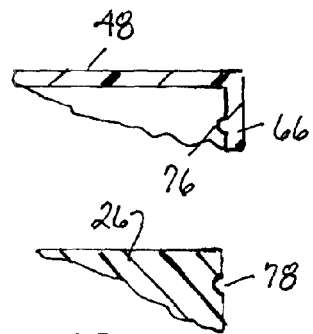
FIG. 13 is a cross section view similar to FIG. 9 showing another embodiment.

FIG. 13 shows flange 66 of cover 48 to have a locating feature 76 on its inner surface. An example of a locating feature is a bead 76 running along the flange parallel with sides of wall 26. When cover 48 is fully seated on wall 26, bead 76 lodges in a groove 78 in the sides of wall 26 which confronts flange 66. The material of the cover has slight flexibility which allows the flange to flex as the cover is being placed on wall 26 and bead 76 rides along the side of wall 26 and the flange to then relax upon the bead coming into registration with the groove. The bead and groove need not extend the full length of a side, and they need not be in all sides. They can be in just enough of the sides to provide a snap-on fit of the cover to the wall without making it too difficult to remove the cover. The flange can serve to locate a sheet like sheet 70 which has a perimeter exactly matching that of top end surface 30 by placing the sheet inside the interior of the cover through the open bottom of the cover so that the sheet is bounded by the flange, and then placing the cover on the model.

Figure 14:
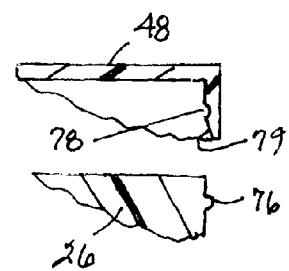
FIG. 14 is a view similar to FIG. 13 showing a variation.

FIG. 14 shows a variation where feature 76 is on the sides of wall 26 and groove 78 is in cover 48. The end of flange 66 has a taper 79 which upon riding across feature 76 will flex the flange slightly outward until groove 78 registers with bead 76 and the flange snaps into place with bead 76 lodging in groove 78.

Figure 15:
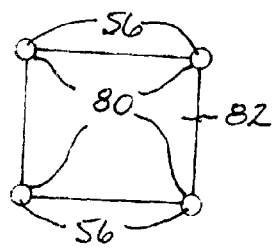
FIG. 15 is a plan view showing a portion of another embodiment.

FIG. 15 shows a rectangular sheet 82 like sheet 62 but having a scallop 80 at each corner with locates to a respective post 56. The posts can be in either wall 26 or cover 48 and fit to holes 60 in the other.

In some dental arch models, the removable cover 30 need not be transparent. For example, the cover can be opaque and indicia may be present in any of one or more forms on at least one of its outer and inner surfaces 52, 54. Such forms of indicia include labels, surface printing, hot stamping, and inscribing. In such models, when it is desired to display different indicia, the entire cover is replaced with one that still fits to the arch model but has different indicia.

Figure 16:
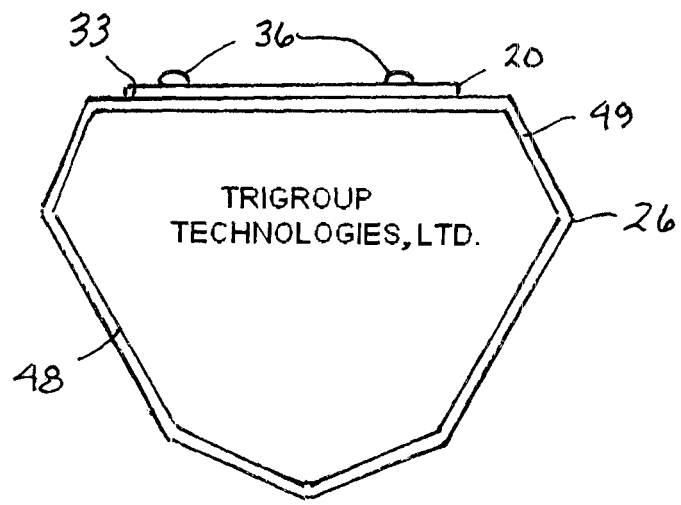
FIG. 16 is a view in the same direction as FIG. 2 showing another embodiment.

FIG. 16 shows an example of this where indicia is disposed on the outer surface of a removable cover 48 which separably attaches to the wall of a dental arch model as previously explained. This cover can be either opaque or transparent.

Figure 17:
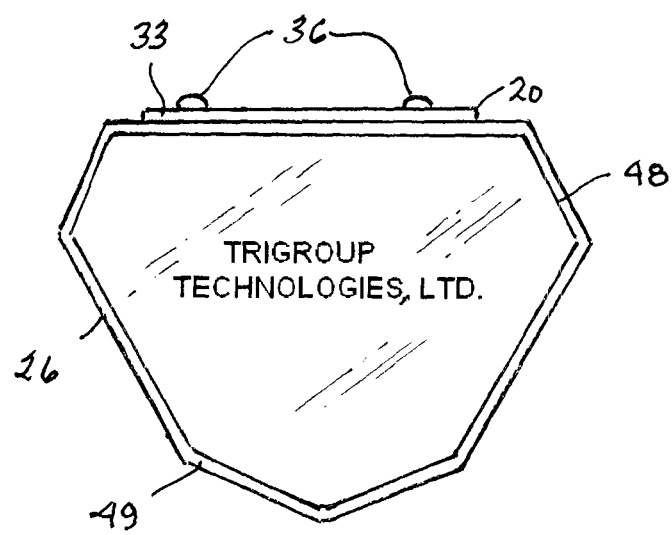
FIG. 17 is a view in the same direction as FIG. 2 showing still another embodiment.

FIG. 17 shows an example where indicia is disposed on the inner surface 54 of a removable cover 48 which separably attaches to the wall of a dental arch model as previously explained. This cover is transparent so that the indicia can be viewed looking through the outer surface of the cover. Although not shown in the Figure, cover 48 may also have indicia on its outer surface 52.

The embodiments which have been described so far use a friction- or a force-fit of the cover to the arch model or in the case of FIGS. 13 and 14 an interference fit. All of those types of fit avoid the use of adhesive. It is possible to use adhesive in an unobtrusive way by making holes 60 deep enough to receive a droplet of adhesive, such as an epoxy, which will make contact with a post 56 when the latter is inserted into the hole and upon setting hold the post in the hole while still allowing the cover to be removed. The cover lacks a flange and thereby allows the cover to be pried off by inserting an edge of a pry between the cover and wall 26. It can be re-attached by using a droplet of adhesive as described.

Another way to separably attach cover 48 to a dental arch model is by making through-holes in cover 48 such as in a pattern like that of holes 60 and then passing headed screws through the through-holes and tightening them in holes 60. The through-holes may have countersinks to allow the screw heads to be substantially flush with the outer surface of the cover when tightened. Polycarbonante is an example of a suitable material for cover 48.

What is claimed is:

1. A model of a single dental arch comprising:
   a wall presenting a top surface and a side surface extending downward from a perimeter of the top surface;
   a model of an oral cavity underlying the wall and containing a model of a gum underlying the wall to the right and left of a medial plane of the oral cavity and of teeth which are set in the gum and extend downwardly from the gum to teeth cusps;
   the top surface having an expanse which comprises a margin extending along the perimeter to occlude the gum both to the right and left of the medial plane; and
   a cover which overlies the top surface and is separably attached to the wall, the cover comprising an inner surface confronting the top surface, an outer surface opposite the inner surface, and indicia disposed on at least one of the inner and outer surfaces.

2. A model of a single dental arch as set forth in claim 1 in which the indicia is disposed on the outer surface.

3. A model of a single dental arch as set forth in claim 1 in which the indicia is disposed on the inner surface and the cover comprises a transparent zone through which the indicia can be viewed.

4. A model of a single dental arch as set forth in claim 1 in which the cover comprises a perimeter which substantially congruently registers with the perimeter of the top surface.

5. A model of a single dental arch as set forth in claim 4 in which one of the cover and the top surface comprises multiple holes, and the other of the cover and the top surface comprises multiple posts extending into the multiple holes via which the cover separably attaches to the wall.

6. A model of a single dental arch as set forth in claim 4 in which the cover further comprises a flange which overlaps the side surface of the wall, and engages the side surface of the wall to separably attach the cover to the wall.

7. A model of a single dental arch as set forth in claim 6 in which one of the flange and the side surface of the wall comprises a bead and the other of the flange and the side surface of the wall comprises a groove which receives the bead to separably attach the cover to the wall.

8. A typodont comprising:
   a model of an oral cavity containing a model of an upper dental arch and a model of a lower dental arch;
   a connection for articulating the arches between closed and open conditions;
   the model of an upper dental arch comprising a model of an upper gum disposed right and left of a medial plane of the oral cavity and of upper teeth which are set in the upper gum and extend downwardly from the upper gum to teeth cusps;
   the model of a lower dental arch comprising a model of a lower gum disposed right and left of the medial plane and of lower teeth which are set in the lower gum and extend upwardly from the lower gum to teeth cusps;
   one of the models of a dental arch comprising a wall, the gum of the one of the models of a dental arch being disposed between the wall and the teeth of the one of the models of a dental arch, the wall comprising a surface which is opposite the gum of the one of the models of a dental arch and which has an expanse which comprises a perimeter margin occluding the gum of the one of the models of a dental arch both to right and left of the medial plane; and
   a cover which overlies the surface and which is separably attached to the wall, the cover comprising an inner surface confronting the surface of the wall, an outer surface opposite the inner surface, and indicia disposed on at least one of the inner and outer surfaces.

9. A typodont as set forth in claim 8 in which the indicia is disposed on the outer surface.

10. A dental arch model as set forth in claim 8 in which the indicia is disposed on the inner surface and the cover comprises a transparent zone through which the indicia can be viewed.

11. A typodont as set forth in claim 8 in which the surface of the wall comprises a continuous perimeter and the cover comprises a continuous perimeter which substantially congruently registers with the continuous perimeter of the surface of the wall.

12. A typodont as set forth in claim 11 in which one of the cover and the surface of the wall comprises multiple holes, and the other of the cover and the surface of the wall comprises multiple posts extending into the multiple holes via which the cover separably attaches to the wall.

13. A typodont as set forth in claim 11 in which the surface of the wall comprises an end surface and a side surface which extends from the continuous perimeter of the wall and the cover further comprises a flange which overlaps the side surface, and engages the side surface to separably attach the cover to the wall.

14. A typodont as set forth in claim 13 in which one of the flange and the side surface comprises a bead and the other of the flange and the side surface comprises a groove which receives the bead to separably attach the cover to the wall.

* * * * *